(12) United States Patent
Barrand

(10) Patent No.: US 8,808,355 B2
(45) Date of Patent: Aug. 19, 2014

(54) STENT GRAFT HAVING A CLOSEABLE FENESTRATION

(71) Applicant: Cook Medical Technologies LLC, Bloomington, IN (US)

(72) Inventor: Zoe Barrand, Greenslopes (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/803,263

(22) Filed: Mar. 14, 2013

(65) Prior Publication Data

US 2014/0148888 A1    May 29, 2014

(30) Foreign Application Priority Data

Nov. 27, 2012   (AU) ................................ 2012258394

(51) Int. Cl.
*A61F 2/06*   (2013.01)

(52) U.S. Cl.
USPC .......................... 623/1.24; 623/1.13; 623/1.23

(58) Field of Classification Search
CPC .............. A61F 2/04; A61F 2/06; A61F 2/07; A61F 2/24; A61F 2007/07–2007/077; A61F 2002/9511; A61F 2002/9528; A61F 2002/2439
USPC .............................. 623/1.13, 1.23–1.31, 1.35
See application file for complete search history.

(56) References Cited

U.S. PATENT DOCUMENTS

| | | | |
|---|---|---|---|
| 8,034,093 B2 * | 10/2011 | Hartley et al. ............... | 623/1.11 |
| 8,167,926 B2 * | 5/2012 | Hartley et al. ............... | 623/1.13 |
| 8,172,895 B2 * | 5/2012 | Anderson et al. ............ | 623/1.23 |
| 8,470,018 B2 * | 6/2013 | Hartley et al. ............... | 623/1.13 |
| 2002/0169497 A1 | 11/2002 | Wholey et al. | |
| 2003/0204243 A1 | 10/2003 | Shiu | |
| 2004/0059406 A1 * | 3/2004 | Cully et al. .................. | 623/1.11 |
| 2005/0059923 A1 * | 3/2005 | Gamboa ....................... | 623/1.16 |
| 2005/0182476 A1 | 8/2005 | Hartley et al. | |
| 2006/0095118 A1 | 5/2006 | Hartley | |
| 2006/0287712 A1 | 12/2006 | Eidenschink | |
| 2007/0123910 A1 | 5/2007 | Hartley et al. | |
| 2007/0250154 A1 | 10/2007 | Greenberg et al. | |
| 2010/0222869 A1 * | 9/2010 | Delaney ........................ | 623/1.26 |

FOREIGN PATENT DOCUMENTS

| | | |
|---|---|---|
| AU | 2011200858 | 3/2011 |
| AU | 2011202120 | 5/2011 |
| JP | 2003250907 | 9/2003 |
| WO | 9853761 | 12/1998 |
| WO | 2008057568 A1 | 5/2008 |
| WO | 2008057569 A1 | 5/2008 |

* cited by examiner

*Primary Examiner* — Kathleen Holwerda
*Assistant Examiner* — Sarah W Aleman
(74) *Attorney, Agent, or Firm* — Richard J. Godlewski; Taiwoods Lin

(57) ABSTRACT

A radially expandable stent graft 10 for placement in a lumen of a patient is disclosed. The stent graft 10 comprises: a prosthetic trunk 100 comprising a trunk lumen 110 there-through; a prosthetic branch 300 comprising a branch lumen 310 extending there-through, wherein the branch lumen 310 is in fluid communication with the trunk lumen 110 through a lateral opening 115 in the trunk lumen 110; a valve 150 comprising a fenestration 152 for providing temporary lateral access into the trunk lumen 110, the valve 150 positioned opposite the lateral opening 115 in the trunk lumen 110; and a valve actuator. The valve actuator closes the fenestration 152 as the stent graft 10 expands.

20 Claims, 16 Drawing Sheets

STENT GRAFT HAVING A CLOSEABLE FENESTRATION

FIELD OF INVENTION

This invention relates to medical devices and more particularly to devices which can be deployed by endovascular means into the vasculature of a patient.

INCORPORATION BY REFERENCE

The entire contents of each of the patent applications listed below are hereby incorporated by reference.
- U.S. patent application Ser. No. 10/962,763 entitled "Introducer for Iliac Side Branch Device"
- PCT Patent Publication No WO 98/53761 entitled "A Prosthesis and a Method of Deploying a Prosthesis"
- U.S. patent application Ser. No. 11/600,655 entitled "Stent Graft Introducer" (US Publication 2007/0123910)
- U.S. patent application Ser. No. 11/788,285 entitled "Twin Bifurcated Stent Graft" (US Publication 2007/0250154)
- Australian Patent Application No 2011202120, filed May 9, 2011 entitled "Paraplegia Prevention Valve For Stent Grafts"
- U.S. patent application Ser. No. 11/231,621 (Published as US2006/0095118) entitled "Side Branch Stent Graft".

BACKGROUND OF THE INVENTION

Some endovascular procedures require stent grafts to have temporary access ports or fenestrations. Various fenestrations have been developed that are openable or closeable and can therefore be described as valved fenestrations. Difficulties with existing valved fenestrations within stent grafts include the space they require and limitations on where they can be placed with respect to expandable stents and bifurcations for instance. Difficulties can arise in design of closing mechanisms for valved fenestrations as well.

Throughout this specification, when discussing the application of this invention to the aorta or other blood vessels, the term "distal" with respect to a prosthesis is intended to refer to a location that is, or a portion of the prosthesis that when implanted is, further downstream with respect to blood flow; the term "distally" means in the direction of blood flow or further downstream. The term "proximal" is intended to refer to a location that is, or a portion of the prosthesis that when implanted is, further upstream with respect to blood flow; the term "proximally" means in the direction opposite to the direction of blood flow or further upstream.

SUMMARY OF THE INVENTION

According to a first aspect of the invention there is provided a radially expandable stent graft for placement in a lumen of a patient, the stent graft comprising:
 a prosthetic trunk comprising a trunk lumen therethrough;
 at least one zig-zag stent extending around the prosthetic trunk, the stent comprising a plurality of struts and bends, the bends being between adjacent struts;
 a valve comprising a fenestration openable into the trunk lumen; and
 a tension member extending from the valve to an anchor point on the prosthetic trunk spaced from the valve, such that radial expansion of the stent graft pulls the tension member so as to close the fenestration.

In one form the valve comprises:
a short length of tubular valve material; and
a valve thread stitched around the valve material so as to close the fenestration when the valve thread is taut.

In one form the valve thread forms the tension member extending from the valve to an anchor point on the prosthetic trunk spaced from the valve.

In one form the stent graft comprises a releasable constraint arrangement constraining the zig-zag stent,
wherein the valve thread is tied to the zig-zag stent such that, release of the constraint arrangement pulls the thread which gathers the valve material so as to close the fenestration.

In one form the releasable constraint arrangement comprises:
 a release wire; and
 a loop of constraining thread, the constraining thread looped around the release wire and a strut of the zig-zag stent, the constraining thread drawn tight and tied to itself,
 whereby the release wire is withdrawable from the loop of constraining thread so cease constraining the zig-zag stent and thereby close the fenestration.

In one form the releasable constraint arrangement comprises:
 a release wire; and
 a loop of constraining thread, the constraining thread looped around the release wire and a strut of the zig-zag stent, the constraining thread drawn tight and tied to itself,
 whereby the release wire is withdrawable from the loop of constraining thread so cease constraining the zig-zag stent and thereby close the fenestration.

In one form the stent graft comprises a pair of tension members, the tension members extending from opposite sides of the valve to respective anchor points. The pair may be symmetrically arranged.

In one form the stent graft comprises a single tension member tied at one end to a first strut of the zig-zag stent and tied at a second end to a second strut of the zig-zag stent, the second end opposite the first end.

In one form the zig-zag stent is super elastic.

According to a second aspect of the invention there is provided a radially expandable stent graft for placement in a lumen of a patient, the stent graft comprising:
 a prosthetic trunk comprising a trunk lumen there-through;
 a prosthetic branch comprising a branch lumen extending there-through, wherein the branch lumen is in fluid communication with the trunk lumen through a lateral opening in the trunk lumen;
 a valve comprising a fenestration openable into the trunk lumen, the valve positioned opposite the lateral opening in the trunk lumen; and
 a valve actuator,
 wherein the valve actuator closes the fenestration as the stent graft expands.

In one form the stent graft comprises:
 at least one zig-zag stent extending around the tubular body, the stent comprising a plurality of struts and bends, the bends being between adjacent struts; and
 a releasable constraint arrangement constraining the zig-zag stent,
 wherein release of the constraint arrangement actuates the valve actuator so as to close the fenestration as the stent graft expands.

In one form the stent graft the valve comprises:
 a short length of tubular valve material; and
 a tension member connected around the valve material so as to close the fenestration when the tension member is taut.

In one form the tension member is a valve thread.

In one form the valve actuator comprises the valve thread extending between the valve and an anchor point on the prosthetic trunk, the anchor point spaced from the valve.

In one form the valve thread is tied to the zig-zag stent such that release of the constraint arrangement pulls the thread which gathers the valve material so as to close the fenestration.

In one form the constraint arrangement comprises:

a release wire extending longitudinally along the prosthetic trunk; and a loop of constraining thread engaged with the release wire and engaged around a portion of the prosthetic trunk circumferentially spaced a selected distance away from the release wire, and drawn tight and tied to itself constraining the zig-zag stent in a compressed condition.

In one form the stent graft comprises a pair of tension members, the tension members extending from opposite sides of the valve to respective anchor points.

In one form the stent graft comprises a single tension member tied at one end to a first strut of the zig-zag stent and tied at a second end to a second strut of the zig-zag stent, the second end opposite the first end.

In one form the zig-zag stent is super elastic.

According to a third aspect of the invention there is provided a radially expandable stent graft for placement in a lumen of a patient, the stent graft comprising:

a prosthetic trunk comprising a trunk lumen there-through;

a prosthetic branch comprising a branch lumen extending there-through, wherein the branch lumen is in fluid communication with the trunk lumen through a lateral opening in the trunk lumen;

a valve comprising a fenestration openable into the trunk lumen, the valve positioned opposite the lateral opening in the trunk lumen, the valve comprising a short length of tubular valve material and a tension member connected around the valve material so as to close the fenestration when the tension member is taut;

a valve actuator;

at least one zig-zag stent extending around the tubular body, the stent comprising a plurality of struts and bends, the bends being between adjacent struts; and a releasable constraint arrangement constraining the zig-zag stent, wherein release of the constraint arrangement actuates the valve actuator so as to close the fenestration as the stent graft expands.

In one form the tension member is a valve thread valve and the actuator comprises the valve thread extending between the valve and an anchor point on the prosthetic trunk, the anchor point spaced from the valve.

A detailed description of one or more embodiments of the invention is provided below along with accompanying figures that illustrate by way of example the principles of the invention. While the invention is described in connection with such embodiments, it should be understood that the invention is not limited to any embodiment. On the contrary, the scope of the invention is limited only by the appended claims and the invention encompasses numerous alternatives, modifications and equivalents. For the purpose of example, numerous specific details are set forth in the following description in order to provide a thorough understanding of the present invention.

The present invention may be practiced according to the claims without some or all of these specific details. For the purpose of clarity, technical material that is known in the technical fields related to the invention has not been described in detail so that the present invention is not unnecessarily obscured.

BRIEF DESCRIPTION OF THE DRAWINGS

To assist with understanding of the invention, reference will now be made to the accompanying drawings which show preferred embodiments of the invention.

In the drawings.

DESCRIPTION OF THE INVENTION

Figure 1A:
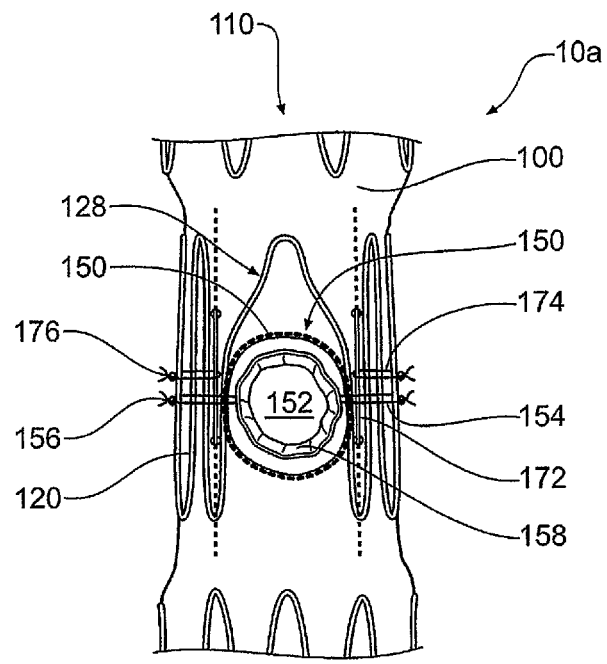
FIGS. 1a and 1b show a first embodiment of a portion of a stent graft according to the invention.
Figure 1B:
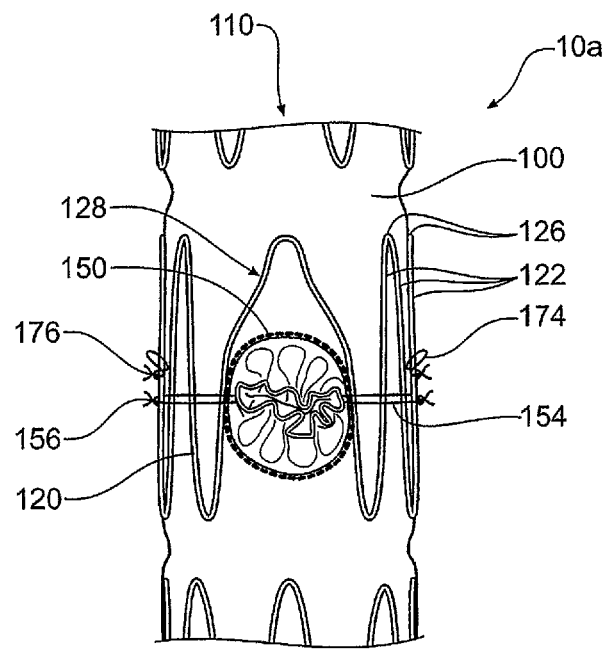

Referring to FIGS. 1a and 1b, a portion of a radially expandable stent graft 10 for placement in a lumen of the patient is shown. The stent graft 10a comprises a prosthetic trunk 100 comprising a trunk lumen 110 therethrough and a plurality of zigzag stents extending around the prosthetic trunk 100. For example, stent 120 has struts 122 and bends 126, as is most clearly shown in FIG. 1b. A valve 150 comprising a fenestration 152 for providing temporary lateral access into the trunk lumen 110 is also provided.

Figure 2A:
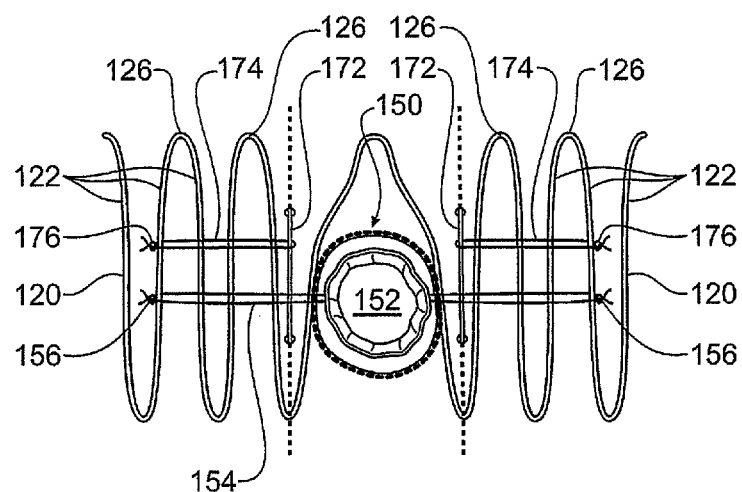
FIGS. 2a and 2b show the embodiment of FIG. 1a but show the stents lying flat, rather than in their actual positions curving circumferentially around the trunk.
Figure 2B:
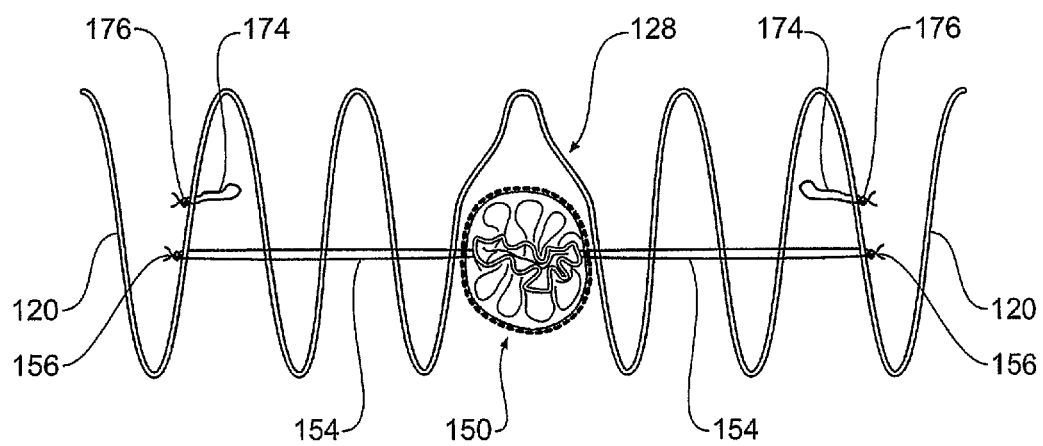

Referring now to FIGS. 2a and 2b, the valve 150 can be seen more clearly. These figures correspond to FIGS. 1a and 1b, but show the stents lying flat, rather than in their actual positions curving circumferentially around the trunk 100. In FIG. 2a, a tension member in the form of a valve thread 154 can be seen extending from the valve 150 to an anchor point 156 on the prosthetic trunk 100 at a position spaced from the valve 150. The valve thread 154 may be a suture. The positioning is such that radial expansion of the stent graft 10 from the position shown in FIG. 2a to the position shown in FIG. 2b pulls the valve thread 154 so as to close the fenestration 152.

The valve 150 comprises a short length of tubular valve material 158 and at least one valve thread 154 stitched around the valve material 158 so as to close the fenestration 152 when the valve thread or suture 154 is taut.

In FIG. 2a, a pair of loops of constraining thread 174 engaged with release wires 172 is shown. When the release wires 172 are removed, the loops of constraining thread 174 come free as is shown in FIG. 2b. This allows the stent 120, to expand so as to pull the valve threads 154 so as to close the fenestration 152.

The use of reducing ties to achieve a reduction in the circumference of the stent graft 10a is known and is explained in the specification of U.S. patent application Ser. No. 11/507,115 entitled "Assembly of Stent Grafts" which is hereby incorporated in its entirety into this specification. With the arrangement shown in FIGS. 1a, 1b, 2a and 2b however, the potential energy of the compressed or constrained stents is used to actuate a valve upon extraction of release wires 172.

Figure 2C:
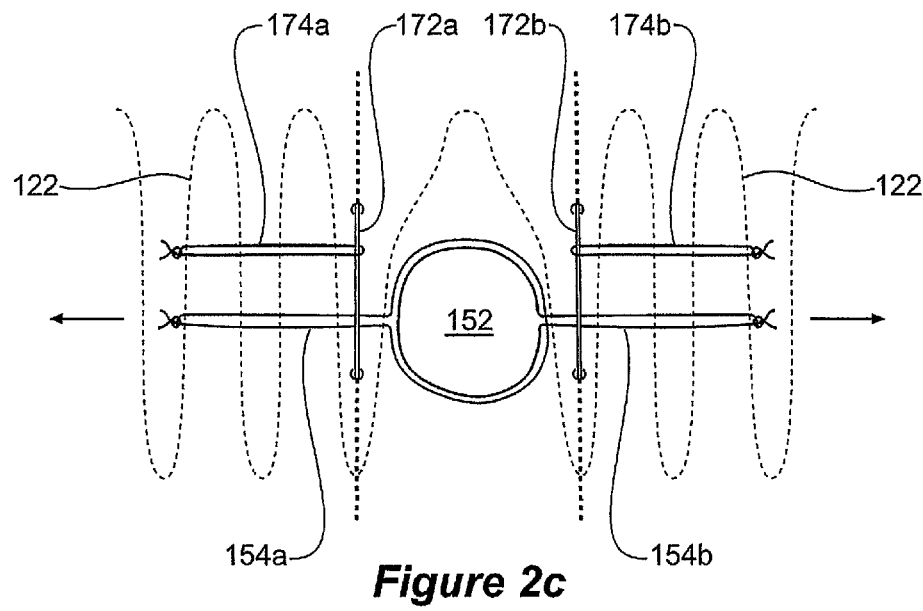
FIG. 2c is similar to FIG. 2a, but removes the valve material to show other elements of a valve actuator in more detail.

With the embodiment shown in FIGS. 2a and 2b, there are a pair of tension members, the tension members extending from opposite sides of the valve to respective anchor points. This is illustrated more clearly in FIG. 2c where paired tension members 154 are labeled 154a and 154b, paired constraining treads 174 are labeled 174a and 174b. There are also a pair of releasable constraint arrangements. Each arrangement is the same. The arrangement on the left hand side of FIG. 2c comprises: a release wire 172a; and a loop of constraining thread 174a, the constraining thread 174a looped around the release wire 172a and a strut 122 of the zig-zag stent. The constraining thread 174a is drawn tight and tied to itself. The release wire 172a is withdrawable from the loop of constraining thread 174a so cease constraining the zig-zag stent 120 and thereby close the fenestration 152. The arrangement on the right hand side of FIG. 2c is a mirror image of the arrangement on the left hand side described above.

Figure 2D:
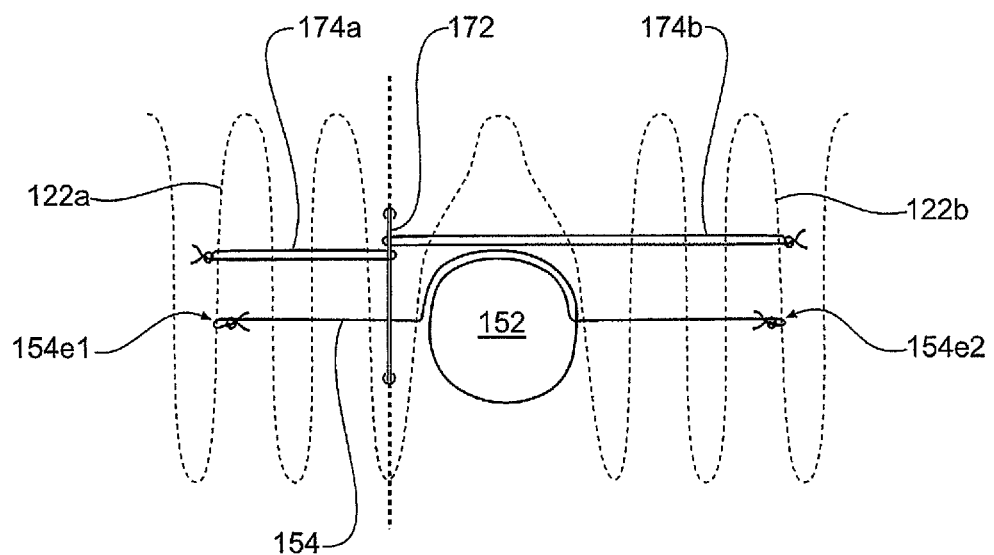
FIG. 2d is similar to FIG. 2c, but shows an second embodiment.

An alternative embodiment is shown in FIG. 2d. With this embodiment, only a single tension member 154 in the form of a valve thread 154 is provided. It can be seen that a single release wire 172 holds a pair of constraining treads 174a, 174b. When this release wire 172 is withdrawn, the spaced apart struts labeled 122a and 122b move apart and pull opposite ends 154e1 and 154e2 thereby closing the fenestration 152. In still further embodiments (not shown) a pair of release wires such as is shown in FIGS. 2a and 2c is be used with a single tension member 154 of the type shown in FIG. 2d. This allows greater control over the closing of the fenestration 152.

With the embodiments illustrated, the expandable stent 120 is a nitinol (metal alloy of nickel and titanium) stent.

Figure 3:
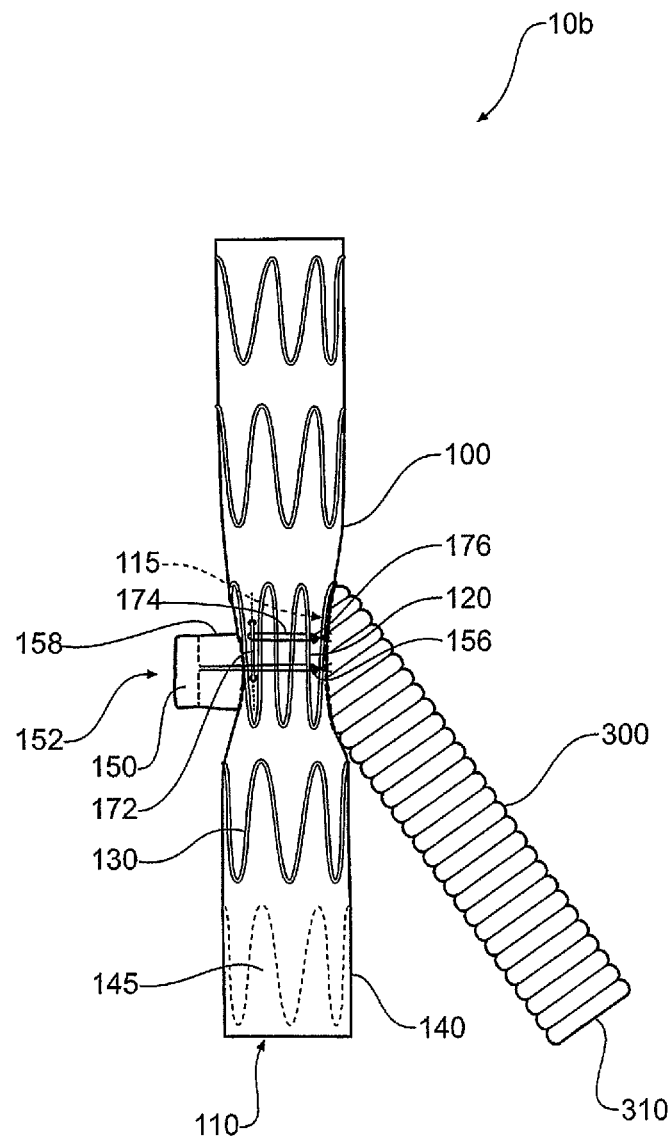
FIG. 3 shows a third embodiment of a stent graft according to the invention.
Figure 4A:
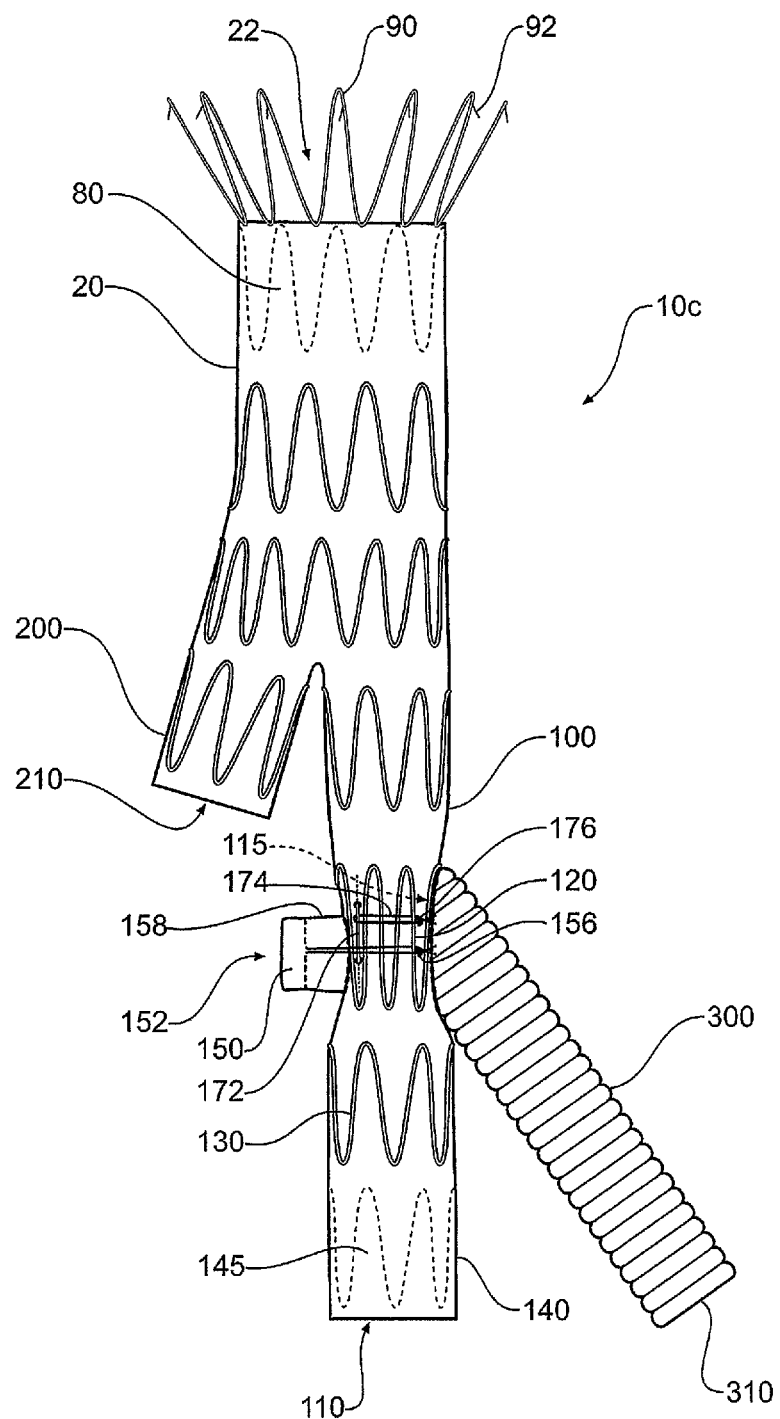
FIGS. 4a and 4c show a fourth embodiment of a stent graft according to the invention.
Figure 4B:
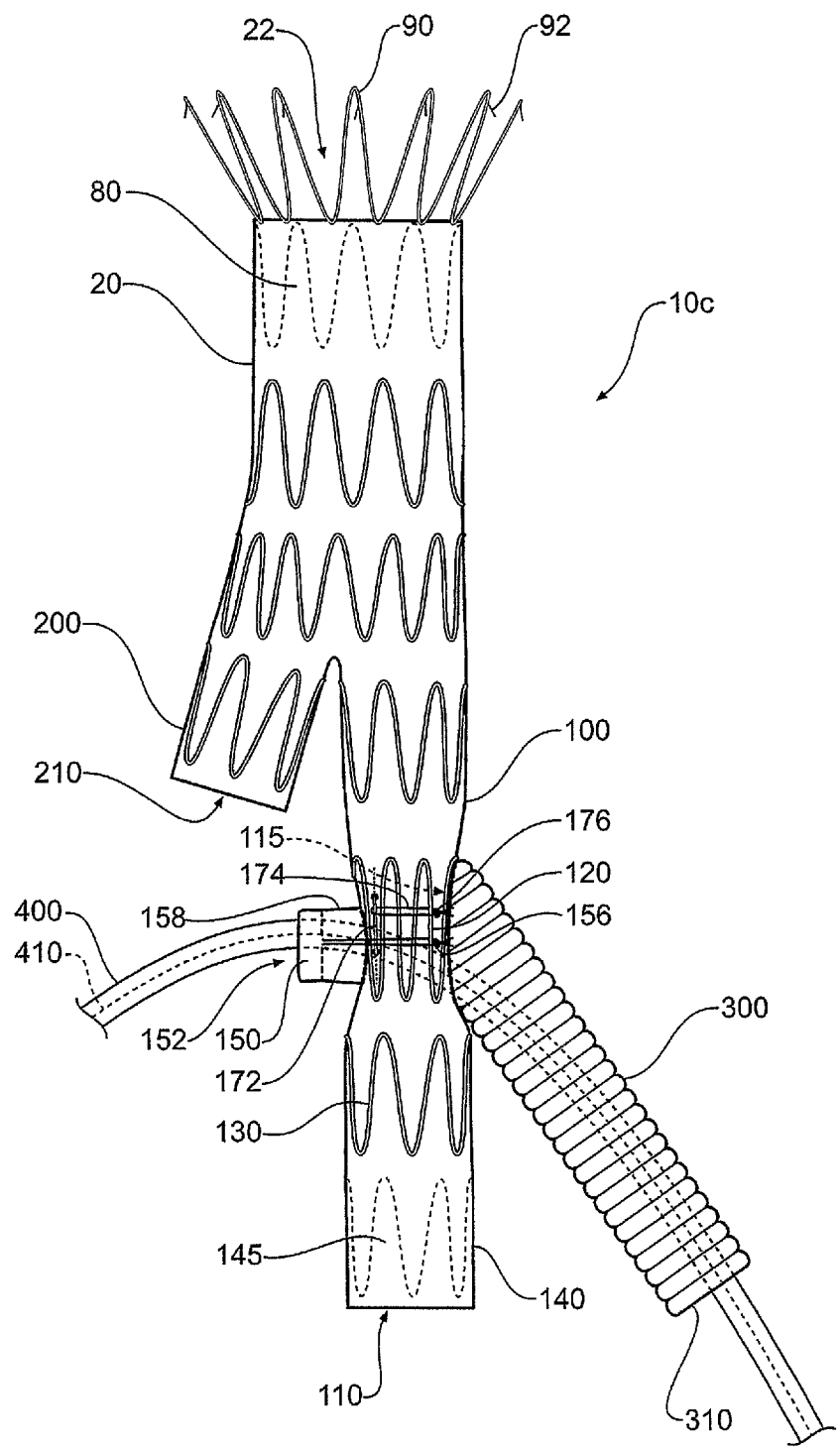
FIG. 4b shows the stent graft of FIGS. 4a and 4c with an indwelling catheter extending through it.
Figure 4C:
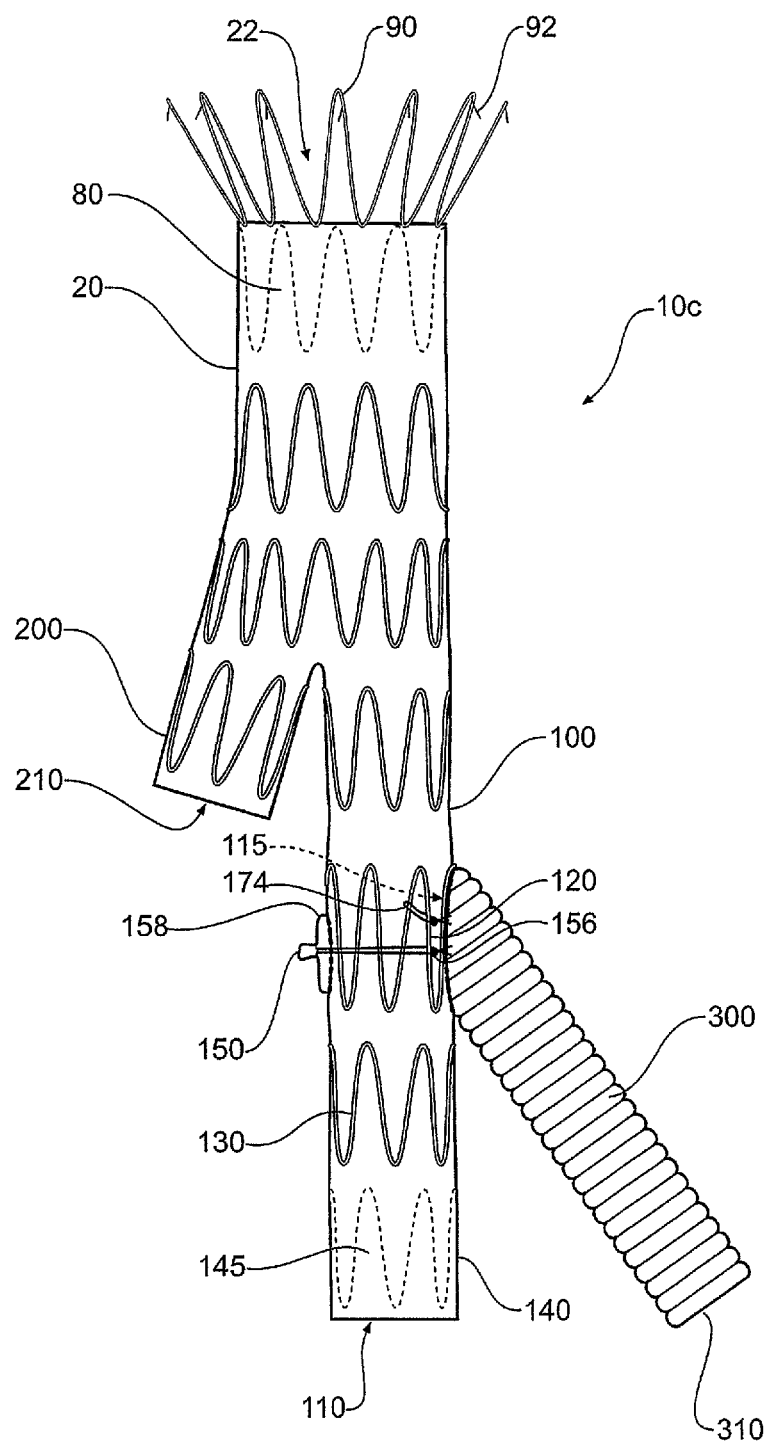

The portion of the radially expandable stent graft 10a shown in FIGS. 1a, 1b, 2a and 2b will have numerous applications and, depending on those applications, may be incorporated into stent grafts of the type shown in FIG. 3 (a third embodiment of the invention) or more complex stent grafts having multiple bifurcations for instance. For example FIGS. 4a to 4c show a bi-branch stent graft 10c according to a fourth aspect of the invention for treating aortoiliac aneurysms.

Figure 5B:
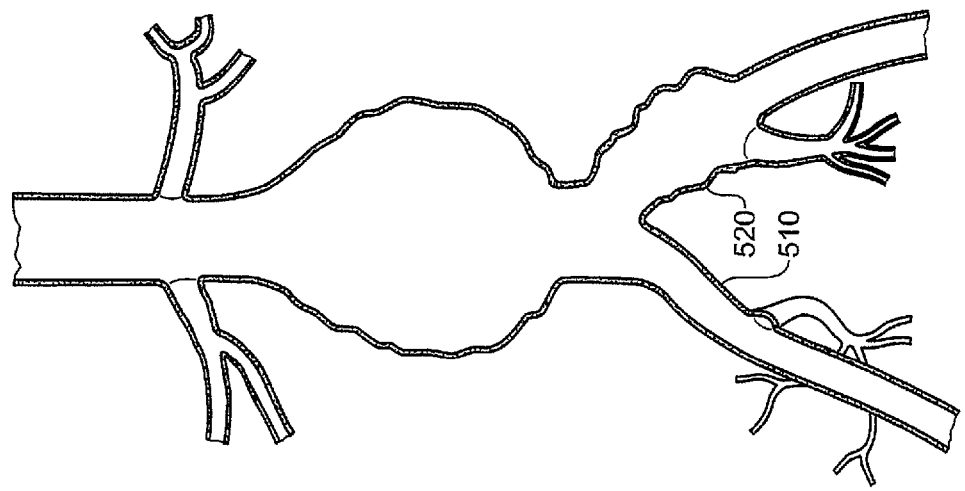
FIG. 5b is similar to FIG. 5a, but shows the vascular of a patient having shorter common iliac arteries.
Figure 5A:
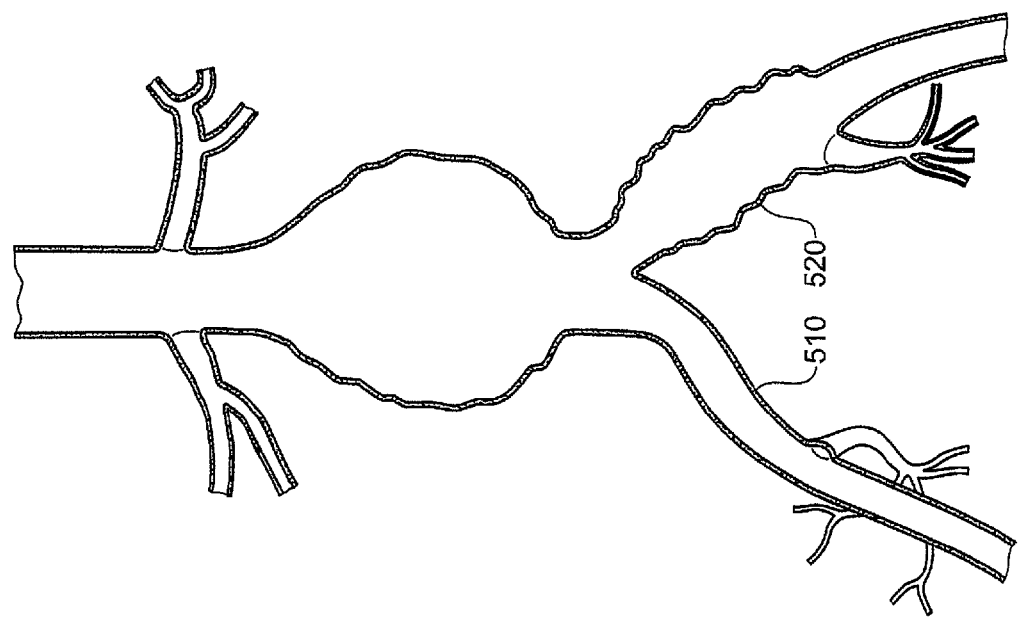
FIG. 5a shows the vascular of a patient having longer common iliac arteries, the vascular having an aortoiliac aneurysm.

FIGS. 5a and 5b show a portion of the vascular system having an aortoiliac aneurysm. FIG. 5a shows the vascular of a patient having longer common iliac arteries 510, 520 and FIG. 5b shows the vascular of a patient having shorter common iliac arteries 510, 520.

There are currently known "bi-Branch" devices that are successful in treating aortoiliac aneurysms in patients with the longer common iliac arteries shown in FIG. 5a (greater than 40 mm in length). Such a device is described U.S. patent application Ser. No. 11/788,285 entitled "Twin Bifurcated Stent Graft" (US Publication 2007/0250154). These devices can be deployed endovascularly using up-and-over sheath access from the contralateral femoral artery to the ipsilateral leg to the ipsilateral internal iliac artery as is described in the aforementioned U.S. patent application Ser. No. 11/788,285.

A limitation of such devices is their inability to adequately treat Asian populations, who commonly have shorter common iliac arteries (less than 40 mm in length) compared to western populations, as illustrated in FIG. 5b.

The access ports currently used on bi-Branch devices for up-and-over sheath access from the contralateral femoral artery to the ipsilateral leg to the ipsilateral internal iliac artery, do not allow for treatment of shorter common iliac arteries (<40 mm in length) due to their positioning on the ipsilateral leg, and cannot readily be repositioned to be opposite the internal opening of the helical side branch.

Figure 5C:
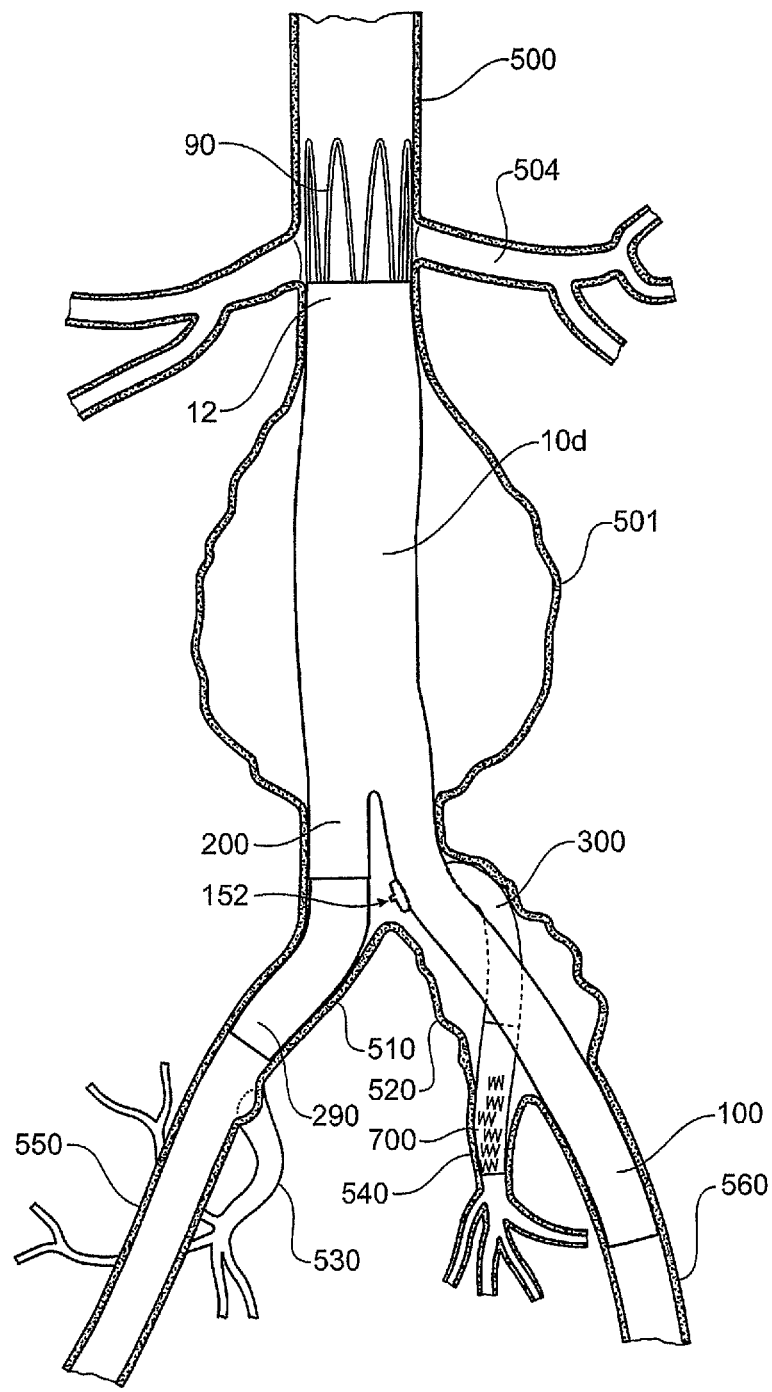
FIG. 5c shows the stent graft of FIGS. 4a-4c deployed within the vascular shown in FIG. 5b.

The fourth embodiment of the invention, in the form of a stent graft 10c shown in FIGS. 4a to 4c, is able to be used to treat populations having shorter common iliac arteries (less than 40 mm in length). FIG. 5c shows such a stent graft 10 deployed.

When the valve 150 is open as is shown in FIG. 4b, minimal resistance is experienced by the physician when tracking a sheath 400 through into the side arm 300, as the valve opening forms a large, unobstructed fenestration 152. Once the valve opening is no longer required, the release wire(s) 172 can be removed. This allows the stent 120 to expand, as is most clearly illustrated progressively from FIG. 2a to FIG. 2b. Radial expansion of the stent 120 graft actuates the valve 150 closed by pulling the valve thread 154 so as to close the fenestration 152 as shown in FIG. 4c.

In the embodiment described above, the tension member 154 is a valve thread. In other embodiments, other tension members such as wire may be used.

FIGS. 6 and 7a to 7d show the various stages of deployment of a stent graft according to the embodiment of the present invention shown in FIGS. 4a to 4c.

Figure 6:
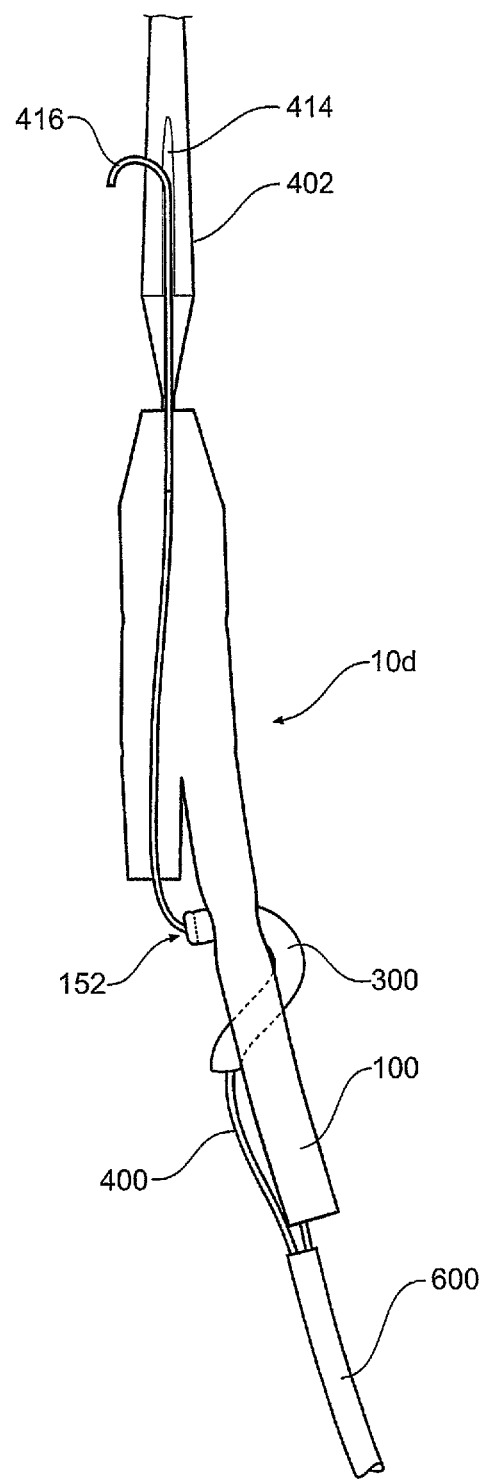
FIG. 6 shows a stent graft according to a fifth embodiment of the invention, that is similar to the stent graft of FIGS. 4a-4c, being loaded onto a delivery device.

FIG. 6 shows a schematic version of an embodiment of a stent graft 10d according to the present invention loaded onto a delivery device. For convenience the sheath of the delivery device has been withdrawn to show the assembly inside it. The delivery device 600 has a nose cone dilator 414 at its proximal end and a stent graft assembly 10d according to a fifth embodiment of the invention is mounted onto the delivery device 600. This embodiment of stent graft 10d has a helical side arm 300 on the longer leg 100 of the stent graft 10d (similar to stent graft 10c shown in FIGS. 4a to 4c). An indwelling catheter 400 extends from the delivery device 600 through the helical side arm 300 exiting at valved fenestration 152 and extending to a groove 414 in the nose cone dilator 402 outside of the stent graft 10. The indwelling catheter 400 has a flexible curved proximal end 416.

The tubular side arm 300 extends around the longer leg 100 and the indwelling catheter 400 extends into the tubular side arm 300 and out through the valved fenestration 152. The valved fenestration 152 is the same as the as the construction shown in FIGS. 4a to 4c.

Figure 7A:
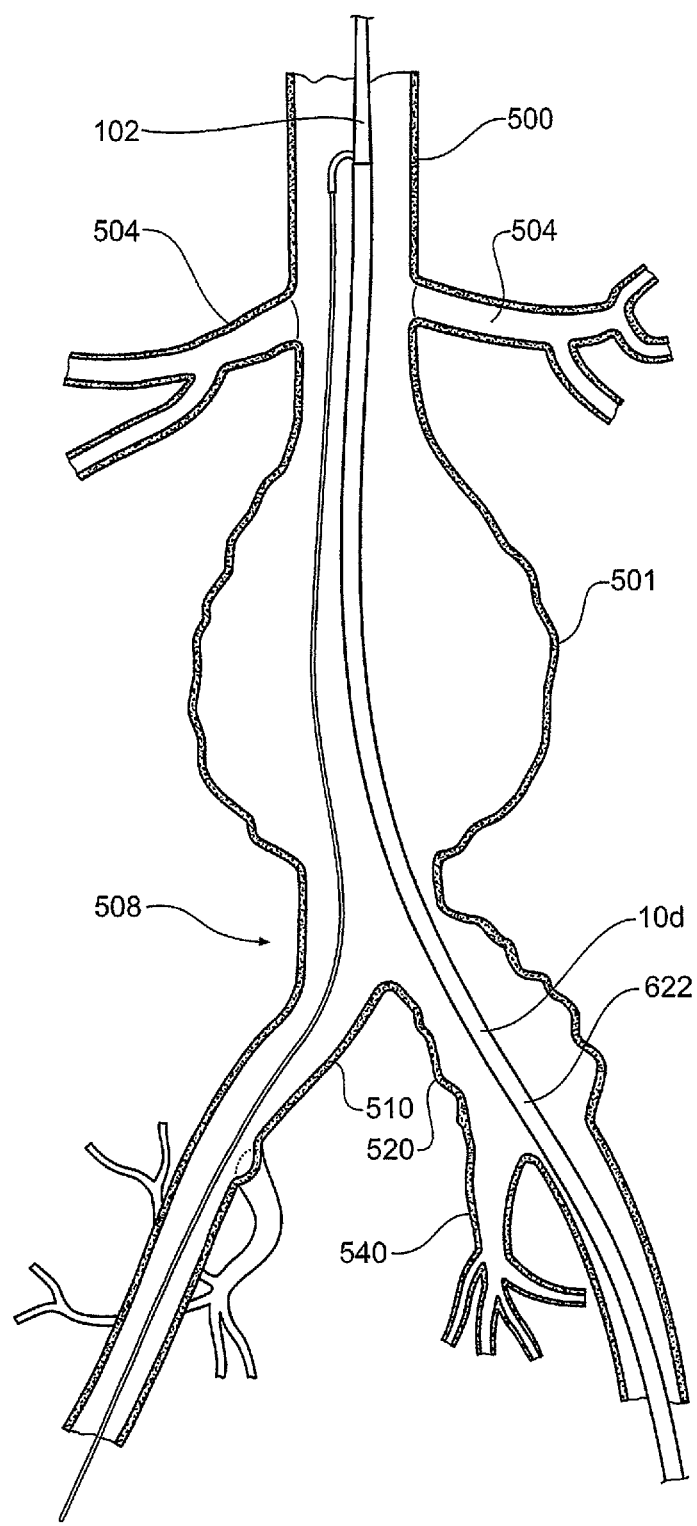
FIGS. 7a to 7f show the various stages of deployment of the stent graft of FIG. 6.

FIG. 7a shows a schematic vasculature of a patient including an aorta 500 renal arteries 504 and an aortic bifurcation 508. Extending from the aortic bifurcation 508 are iliac arteries 510 and 520. The aorta has an aneurysm which extends down the common iliac artery to the position of the internal iliac artery 540. The iliac bifurcation defines the bifurcation between the internal iliac artery 540 and the external iliac artery 560.

FIG. 7a also shows the delivery device 600 with the nose cone dilator 402 proximal of the renal arteries 504 with the indwelling guide wire 490 drawn up into the aorta 500. The process of getting the delivery device 600 into this position, using the indwelling catheter with a curved tip shown in FIG. 6 to facilitate snaring from a contralateral iliac artery, is taught in U.S. patent application Ser. No. 11/788,285 entitled "Twin Bifurcated Stent Graft" (US Publication 2007/0250154).

The sheath 622 of the delivery device 600 is then withdrawn to release the shorter leg of the stent graft 200.

The indwelling catheter is then withdrawn down into the contra-lateral iliac artery 510 and the sheath 622 is withdrawn so that it is distal of the distal end of the side arm 300 while still retaining the distal end of the longer leg 100. This is shown in detail in FIG. 7*b*.

Figure 7B:
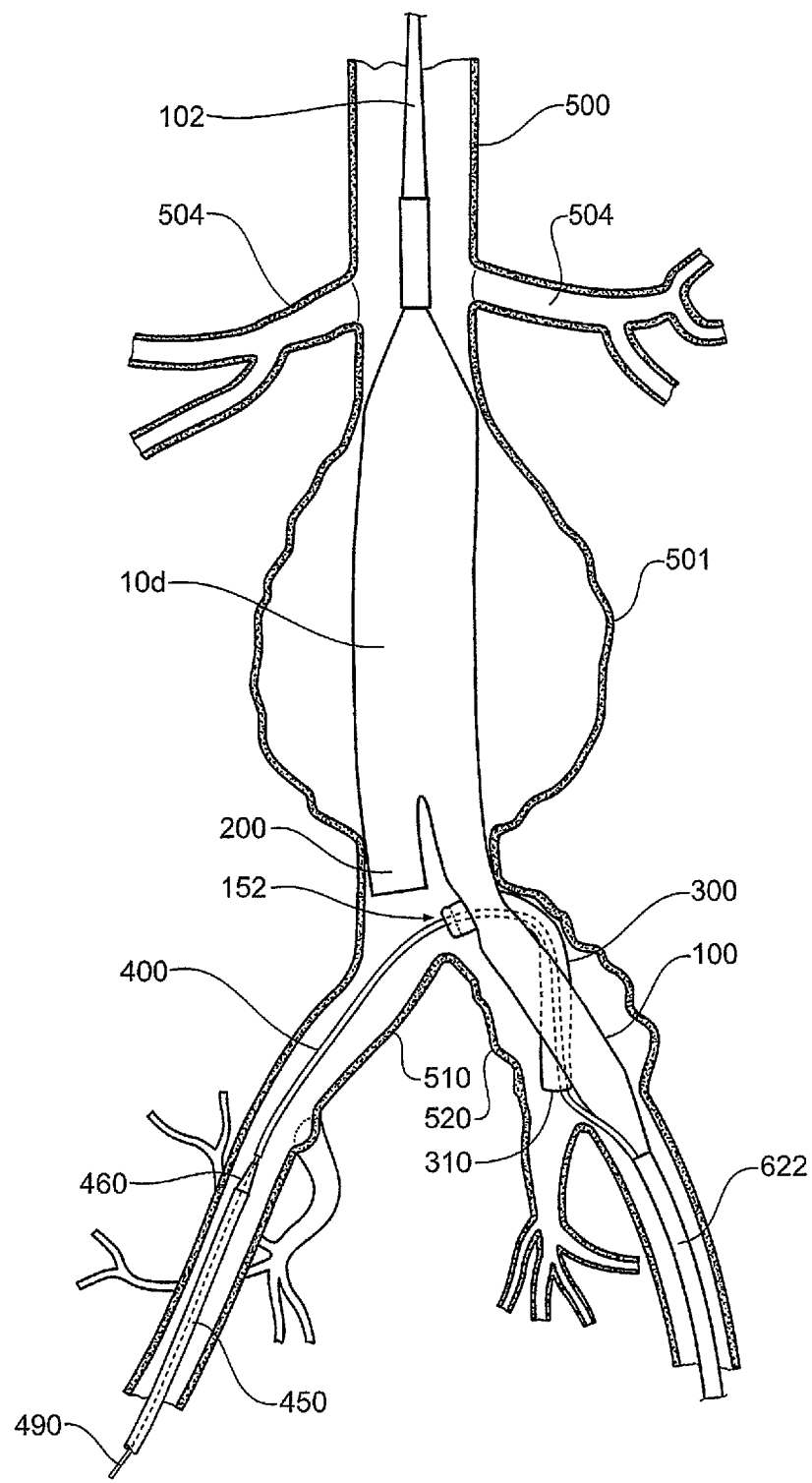
Figure 7C:
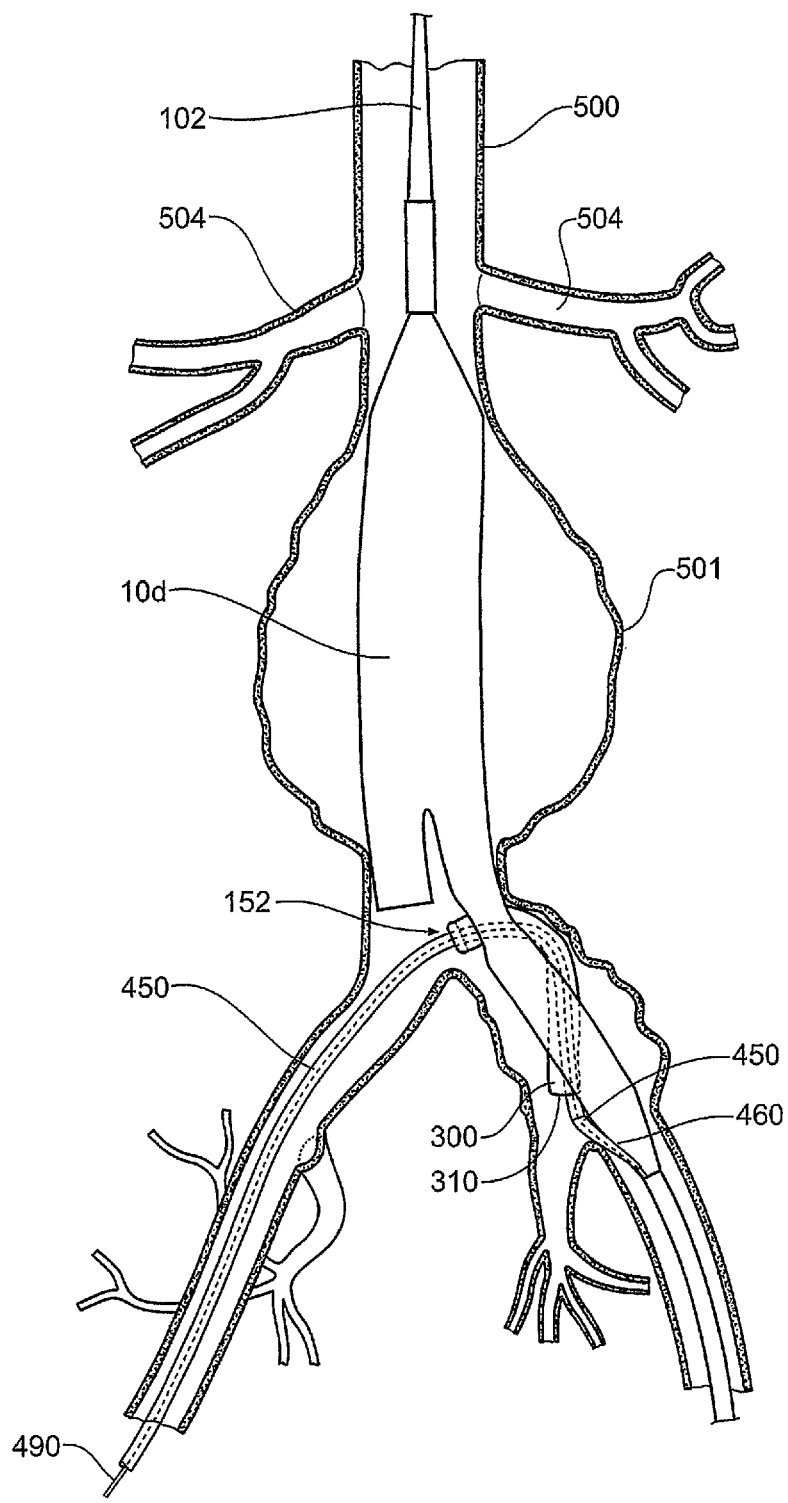
Figure 7D:
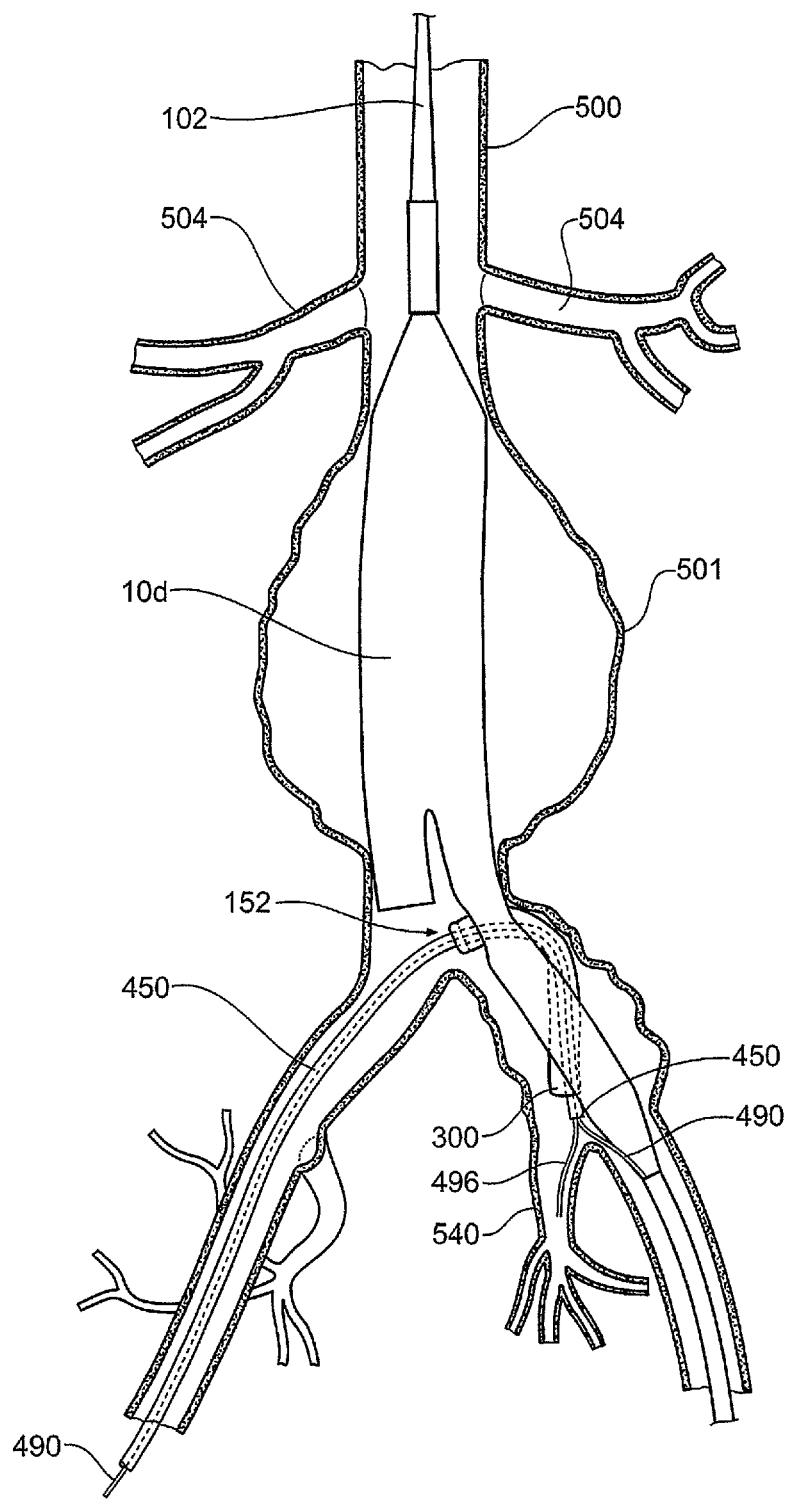

As shown in FIG. 7*b* a dilator and sheath introducer 450 is advanced over the guide wire 490 in the contra-lateral iliac artery 510 and the indwelling catheter 400 and extension arm deployment device are tracked over the guide wire 490 so that the nose cone 460 of the sheath introducer enters the valved fenestration 152 and tracks over the guide wire 490 into the side arm 300 until it exits the distal end of the side arm as shown in FIG. 7*c*. The sheath introducer nose cone 460 is then withdrawn leaving the sheath 450 in place. At this stage the indwelling guide wire 490 is still in a through-and-through position. As shown in FIG. 7*d*, another guide wire 496 is introduced through the sheath 450 and extended from the sheath 450 to enter into the internal iliac artery 540.

Figure 7E:
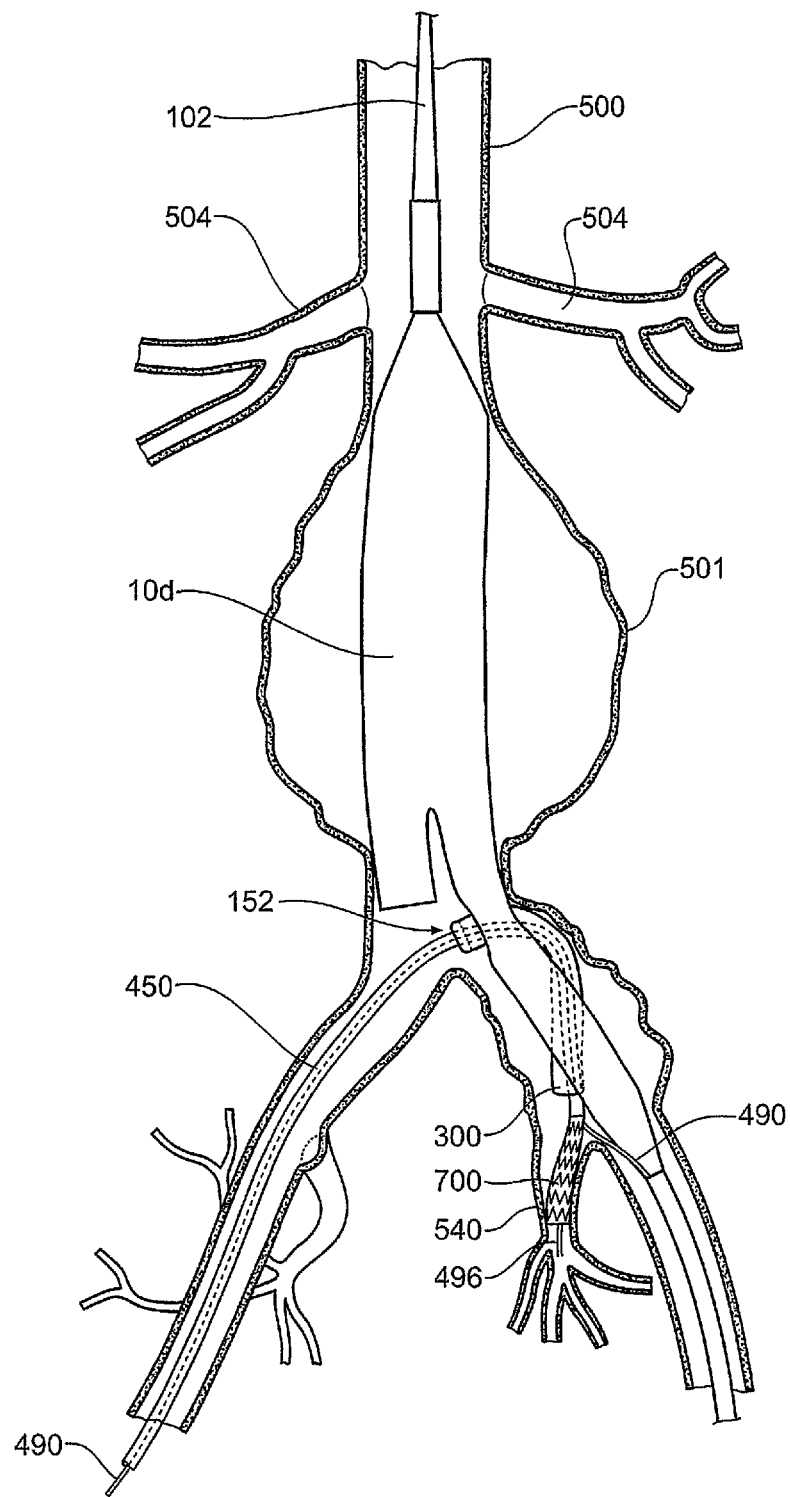
Figure 7F:
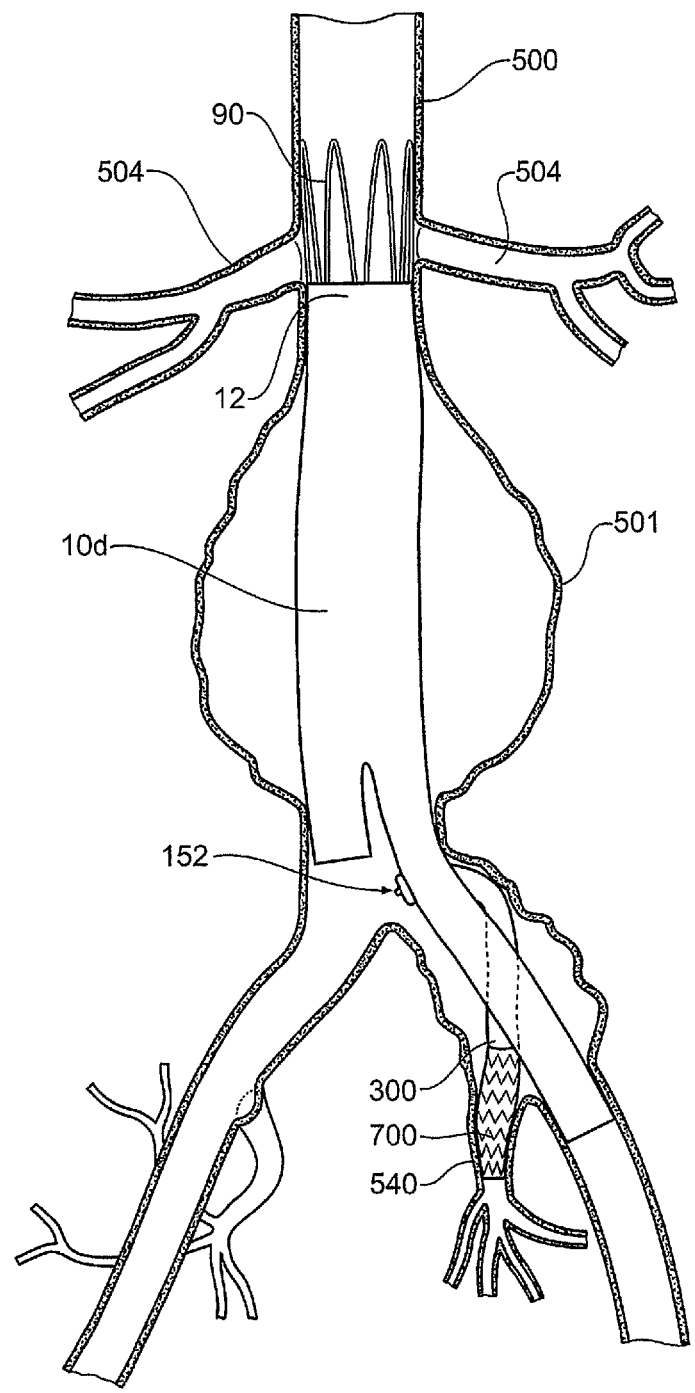

As shown in FIG. 7*e* a side arm deployment device is deployed over the guide wire 496 into the internal iliac artery 540 so that balloon expandable covered stent 700 extends into the internal iliac artery 540 from the side arm 300. The indwelling guide wire 490 is then removed and the position of the distal end of the longer leg 100 is set into the external iliac artery 260 and the balloon expandable covered stent 700 is expanded The final positions are shown in FIGS. 7*f* and 5*c*. To achieve these position, the sheath 450 is withdrawn and the valve 152 is closed by removing the release wires 172 as is shown in FIG. 7*f*. The proximal end of the stent graft is also released from the delivery device 600 such that a portion of the graft seals into a non-aneurysed portion of the aorta 500 distal of the renal arteries 504 while an uncovered suprarenal stent 90 extends over the renal arteries to provide secure fixation. A leg extension 290 may then be placed into the short leg 200 of the graft 10 as is shown if FIG. 5*c*.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A radially expandable stent graft for placement in a lumen of a patient, the stent graft comprising:
   a prosthetic trunk comprising a trunk lumen therethrough;
   at least one zig-zag stent extending around the prosthetic trunk, the stent comprising a plurality of struts and bends, the bends being between adjacent struts;
   a valve comprising a fenestration openable into the trunk lumen; and
   a tension member extending from the valve to an anchor point on the prosthetic trunk spaced from the valve, such that radial expansion of the stent graft pulls the tension member so as to close the fenestration.

2. The stent graft of claim 1, wherein the valve comprises:
   a short length of tubular valve material; and
   a valve thread stitched around the valve material so as to close the fenestration when the valve thread is taut.

3. The stent graft of claim 2, wherein the valve thread forms the tension member extending from the valve to an anchor point on the prosthetic trunk spaced from the valve.

4. The stent graft of claim 3, comprising a releasable constraint arrangement constraining the zig-zag stent, wherein the valve thread is tied to the zig-zag stent such that, release of the constraint arrangement pulls the thread which gathers the valve material so as to close the fenestration.

5. The stent graft of claim 4, wherein the releasable constraint arrangement comprises:
   a release wire; and
   a loop of constraining thread, the constraining thread looped around the release wire and a strut of the zig-zag stent, the constraining thread drawn tight and tied to itself,
   whereby the release wire is withdrawable from the loop of constraining thread so cease constraining the zig-zag stent and thereby close the fenestration.

6. The stent graft of claim 5, comprising a single tension member tied at one end to a first strut of the zig-zag stent and tied at a second end to a second strut of the zig-zag stent, the second end opposite the first end.

7. The stent graft of claim 6, wherein the constraint arrangement comprises:
   a release wire extending longitudinally along the prosthetic trunk; and
   a loop of constraining thread engaged with the release wire and engaged around a portion of the prosthetic trunk circumferentially spaced a selected distance away from the release wire, and drawn tight and tied to itself constraining the zig-zag stent in a compressed condition.

8. The stent graft of claim 7, comprising a single tension member tied at one end to a first strut of the zig-zag stent and tied at a second end to a second strut of the zig-zag stent, the second end opposite the first end.

9. The stent graft of claim 1, comprising a pair of tension members, the tension members extending from opposite sides of the valve to respective anchor points.

10. The stent graft of any of claim 9, wherein the zig-zag stent is super elastic.

11. A radially expandable stent graft for placement in a lumen of a patient, the stent graft comprising:
    a prosthetic trunk comprising a trunk lumen there-through;
    a prosthetic branch comprising a branch lumen extending there-through, wherein the branch lumen is in fluid communication with the trunk lumen through a lateral opening in the trunk lumen;
    a valve comprising a fenestration openable into the trunk lumen, the valve positioned opposite the lateral opening in the trunk lumen; and
    a valve actuator,
    wherein the valve actuator closes the fenestration as the stent graft expands.

12. The stent graft of claim 11, comprising:
    at least one zig-zag stent extending around the tubular body, the stent comprising a plurality of struts and bends, the bends being between adjacent struts; and
    a releasable constraint arrangement constraining the zig-zag stent,
    wherein release of the constraint arrangement actuates the valve actuator so as to close the fenestration as the stent graft expands.

13. The stent graft of claim 12, wherein the valve comprises:
    a short length of tubular valve material; and
    a tension member connected around the valve material so as to close the fenestration when the tension member is taut.

14. The stent graft of claim 13, wherein the tension member is a valve thread.

15. The stent graft of claim 14, wherein the valve actuator comprises the valve thread extending between the valve and an anchor point on the prosthetic trunk, the anchor point spaced from the valve.

16. The stent graft of claim 15, wherein the valve thread is tied to the zig-zag stent such that release of the constraint arrangement pulls the thread which gathers the valve material so as to close the fenestration.

17. The stent graft of claim 11, comprising a pair of tension members, the tension members extending from opposite sides of the valve to respective anchor points.

18. The stent graft of any of claim 17, wherein the zig-zag stent is super elastic.

19. A radially expandable stent graft for placement in a lumen of a patient, the stent graft comprising:
   a prosthetic trunk comprising a trunk lumen there-through;
   a prosthetic branch comprising a branch lumen extending there-through, wherein the branch lumen is in fluid communication with the trunk lumen through a lateral opening in the trunk lumen;
   a valve comprising a fenestration openable into the trunk lumen, the valve positioned opposite the lateral opening in the trunk lumen, the valve comprising a short length of tubular valve material and a tension member connected around the valve material so as to close the fenestration when the tension member is taut;
   a valve actuator;
   at least one zig-zag stent extending around the tubular body, the stent comprising a plurality of struts and bends, the bends being between adjacent struts; and
   a releasable constraint arrangement constraining the zig-zag stent,
   wherein release of the constraint arrangement actuates the valve actuator so as to close the fenestration as the stent graft expands.

20. The stent graft of claim 19, wherein the tension member is a valve thread valve and the actuator comprises the valve thread extending between the valve and an anchor point on the prosthetic trunk, the anchor point spaced from the valve.

* * * * *